(12) United States Patent
Sklebitz

(10) Patent No.: US 6,658,085 B2
(45) Date of Patent: Dec. 2, 2003

(54) MEDICAL EXAMINATION INSTALLATION WITH AN MR SYSTEM AND AN X-RAY SYSTEM

(75) Inventor: Hartmut Sklebitz, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 09/923,836

(22) Filed: Aug. 6, 2001

(65) Prior Publication Data

US 2003/0103597 A1 Jun. 5, 2003

(30) Foreign Application Priority Data

Aug. 4, 2000 (DE) .......................................... 100 38 176

(51) Int. Cl.[7] .......................... G01N 23/04; H01J 35/14
(52) U.S. Cl. ......................... 378/63; 378/137; 378/138
(58) Field of Search ................................ 600/410, 411; 378/4, 63, 137, 138

(56) References Cited

U.S. PATENT DOCUMENTS

| | | | | |
|---|---|---|---|---|
| 5,550,889 A | * | 8/1996 | Gard et al. ................. | 378/113 |
| 5,713,357 A | * | 2/1998 | Meulenbrugge et al. .... | 600/411 |
| 5,807,254 A | * | 9/1998 | Meulenbrugge et al. .... | 600/411 |
| 5,818,901 A | * | 10/1998 | Schulz ........................ | 378/63 |
| 6,263,043 B1 | * | 7/2001 | Maschke .................... | 378/63 |
| 6,385,480 B1 | * | 5/2002 | Bachus et al. ............. | 600/411 |

FOREIGN PATENT DOCUMENTS

WO  WO 96/00520  1/1996

* cited by examiner

Primary Examiner—Edward J. Glick
Assistant Examiner—Allen C Ho
(74) Attorney, Agent, or Firm—Schiff Hardin & Waite

(57) ABSTRACT

A medical examination installation has an MR system and an X-ray system that has an X-ray radiator with an X-ray tube and a solid-state X-ray image detector for producing X-ray exposures. The X-ray system has sensors for the acquisition of the location dependency of the stray field of the MR system in the three spatial axes, and coils for compensation of the stray field, and a computer that uses the output signal of the sensors to calculate a current for the coils which cause the stray field to be reduced in the region of the electron beams of the X-ray tube.

13 Claims, 4 Drawing Sheets

MEDICAL EXAMINATION INSTALLATION WITH AN MR SYSTEM AND AN X-RAY SYSTEM

BACKGROUND OF THE INVENTION

1. Field of the Invention

The present invention is directed to a medical examination installation with an MR system and an X-ray system that has an X-ray radiator with an X-ray tube and a solid-state X-ray image detector for producing X-ray exposures.

2. Description of the Prior Art

Real-time monitoring of interventional medical procedures is necessary, in order to ensure that the procedure is proceeding as intended, and as well as to ensure that any medical instruments which are being employed are precisely positioned at the correct location in the patient.

Magnetic resonance (MR) imaging is a proven diagnostic method that enables tomograms and three-dimensional (3D) reconstructions to be produced. The examination time, however, is relatively long and lies on the order of magnitude of several minutes. For specific examinations, it is meaningful for shortening the exposure time and/or for planning the further execution of the MR examinations to prepare an X-ray exposure before and/or during the MR examination. The quality of the diagnosis is additionally enhanced as a result.

Although such MR systems can fundamentally make the 3D location information required therefor available, there are situations wherein it is desirable to have better access to the patient during the intervention than that afforded by the gantry of an MR system with superconductive magnet or even by a C-shaped magnet apparatus (open). When the patient is moved out of the gantry of the inner magnet region of the MR apparatus for the time of the intervention, for example, an open surgical intervention or the introduction of a biopsy needle can be enabled or simplified. Moreover, monitoring of the patient is improved in this way, for example the delivery of respiratory gasses, infusion tubes as well as a general monitoring of the condition of the patient.

However, organs can dislocate in the intervention due to the pressure of an interventional or surgical tool such as, for example, a biopsy needle or a catheter, so that the current organ position can deviate from the position at the earlier point in time of an MR image acquisition.

For these reasons, it is advantageous when an additional X-ray system—optimally with real-time image acquisition in the fluoroscopic mode or during transillumination—is integrated in an MR apparatus so that a relationship of the local information between the acquired X-ray images to the MR images is possible. An intervention with enhanced certainty thus is possible without delay and with the involvement of the images of both modalities. It is especially advantageous when the X-ray system can make images with 3D information available that can be correlated with the MR images.

PCT Application WO 96/00520 discloses a medical examination installation with an MR system and an independent X-ray system wherein an Independent X-ray device is provided in addition to an Independent MR device. The X-ray device has a voltage supply as well as a C-arm with an X-ray source and the X-ray detector, which form an X-ray unit. A patient lying on a patient support is transported back and forth between the MR device and the X-ray device. The X-ray detector can be a large-area solid-state image converter.

Conventional X-ray real-time image systems with X-ray tubes can be employed only conditionally at MR systems because the stray magnetic field of the MR apparatus does not allow a disturbance-free operation of the X-ray tubes, even though the magnetically deflectable electrons exhibit high speeds over short oath distances.

In the aforementioned POT Application WO 96/00520, for example, it is taught to align the electron path in the X-ray tube according to the magnetic field lines in the proximity of the MR magnet. This alignment of the electron oath functions only at a fixed distance of the MR apparatus from the X-ray tube because the angle of the magnetic field lines changes with the distance from the MR apparatus. Additionally, the tilt of the axis of the X-ray tube relative to the axis of the MR apparatus reduces the usable emission angle of the X-ray tube, and thus the field of view.

SUMMARY OF THE INVENTION

An object of the present invention is to provide a medical diagnostics installation such that an online X-ray system is possible directly at the MR apparatus without influencing the electron oath in the X-ray tube with the magnetic field lines of the MR magnet even given changes in the position or attitude of the X-ray tube.

This object is inventively achieved in a medical examination installation having sensors which identify the magnetic, location-dependent stray field of the MR system in the three spatial axes, a computer determines the coil currents, and coils operated by the computer which compensate the stray field.

It has proven advantageous for the X-ray system to have magnetic field sensors for acquiring the magnetic, location-dependent stray field of the MR system in the three spatial axes.

The magnetic stray field can already be reduced when the X-ray system has a magnetic shielding for the X-ray tube within which the sensors for acquiring the location dependency of the remaining magnetic stray field and within which the coils are arranged.

It has proven advantageous to employ three coil pairs arranged such that their axes respectively reside perpendicularly relative to one another, the coil pairs being arranged in the three spatial axes.

Alternatively, the sensors for the acquisition of the location dependency of the stray field of the MR system in the three spatial axes can be location sensors that determine the position of the X-ray tube in view of the MR system and calculate the magnetic, location-dependent stray field of the MR system at the location of the X-ray tube on the basis of stored magnetic field profiles.

A compact structure derives when the X-ray system is directly attached to the MR apparatus, and the X-ray radiator and the solid-state image detector can be mounted to a C-arm attached to the MR system. The X-ray system alternatively can be mounted to stands directly next to the MR apparatus.

As an alternative, the X-ray radiator and the solid-state X-ray image detector can be secured independently of one another, with location sensors for determining position and angle attached to the X-ray radiator and the solid-state X-ray image detector. The X-ray radiator and the solid-state X-ray image detector are aligned relative to one another and readjusted by motor drives and electronic controls. The position and alignment of X-ray radiator and solid-state X-ray image detector are monitored by the location sensors, so that a so-called "electronic C-arm is achieved. The measurement sensor mechanism with path sensors and rotational angle sensors assures that the current, exact position of the X-ray system in relation to the MR apparatus, particularly relative to the position of the patient support thereof and of the individual components relative to one another is known, so that the components can be reliably and precisely moved on the desired paths.

Spatial information of tomosynthesis images can be linked with the content of stored MR images according to the image fusion technique when the X-ray system is fashioned such that, for producing exposures from a number of projections for tomosynthesis tomograms, X-ray radiator and/or solid-state X-ray image detector are moved on a plane parallel thereto, and when the workstation is configured such that the tomosynthesis tomograms and MR images are superimposed.

It has proven advantageous when the solid-state X-ray image detector is arranged to be displaceable in the patient support.

DESCRIPTION OF THE PREFERRED EMBODIMENTS

Figure 1:
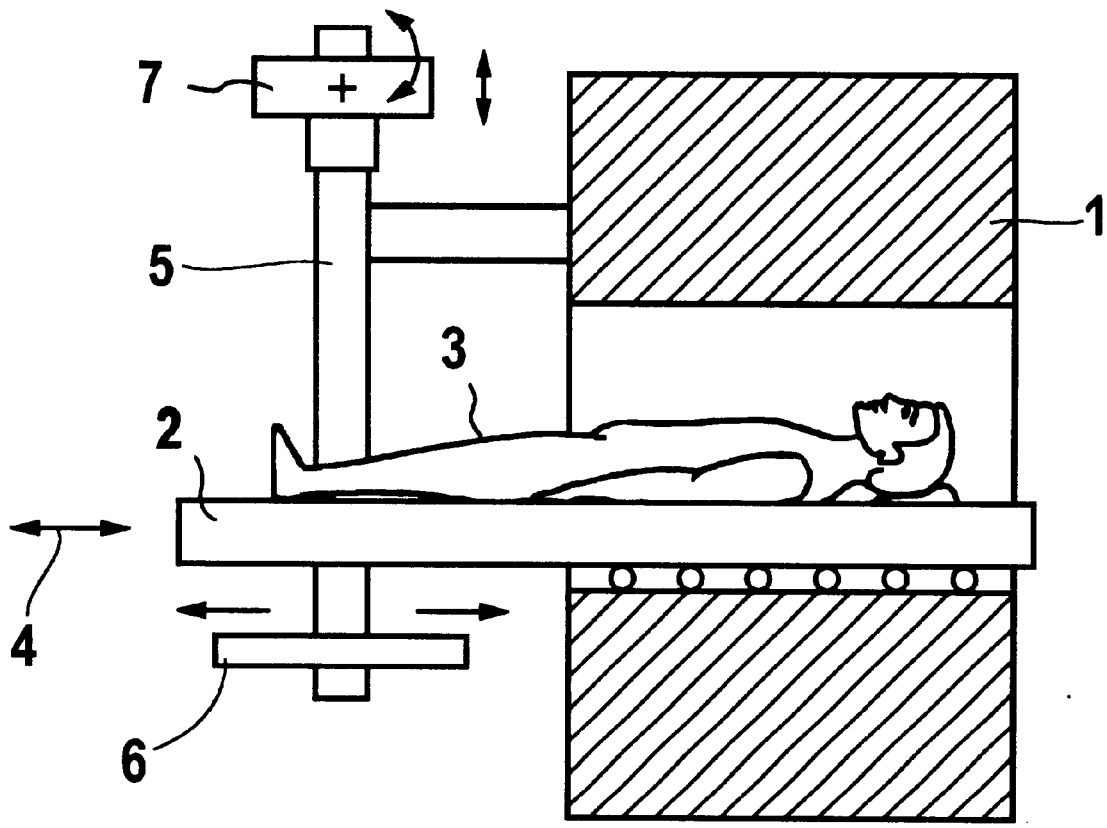
FIG. 1 illustrates a first embodiment of a medical examination installation of the invention with various patient positions.

FIG. 1 schematically shows an MR apparatus 1 with a patient support 2 on which a patient 3 is situated. The patient support 2 is arranged to be movable in the inside of the MR apparatus 1 in the length thereof in the direction of the double arrow 4. An X-ray device is provided having a C-arm 5 that can be attached to the MR apparatus 1. The C-arm 5 has a digital X-ray image detector 6 and an X-ray radiator 7 mounted at its opposite ends for producing X-ray exposures. The digital X-ray image detector 6 can, for example, be a flat solid-state X-ray image detector that is based on an a-Si panel with image points arranged in a matrix. For producing digital X-ray exposures, the patient support 2 can be displaced from the MR apparatus 1 into the X-ray device without repositioning the patient.

Since a-Si panels operate independently of magnetic fields, they can be operated close to the MR device 1, so that they can be secured to the MR apparatus 1 together with the X-ray radiator 7.

Good access to the patient is assured as a result of the fastening of the panel and the X-ray radiator 7 to the C-arm 5 at the MR apparatus 1.

The MR apparatus 1 can be an open system with lateral access to the patient, a closed system—as shown—or a system having two parts axially arranged at a distance from one another, referred to as an interventional MR system, between which access to the patient is possible. It is thereby possible, for example, to prepare a lung exposure by application of the X-radiation between these parts.

Figure 2:
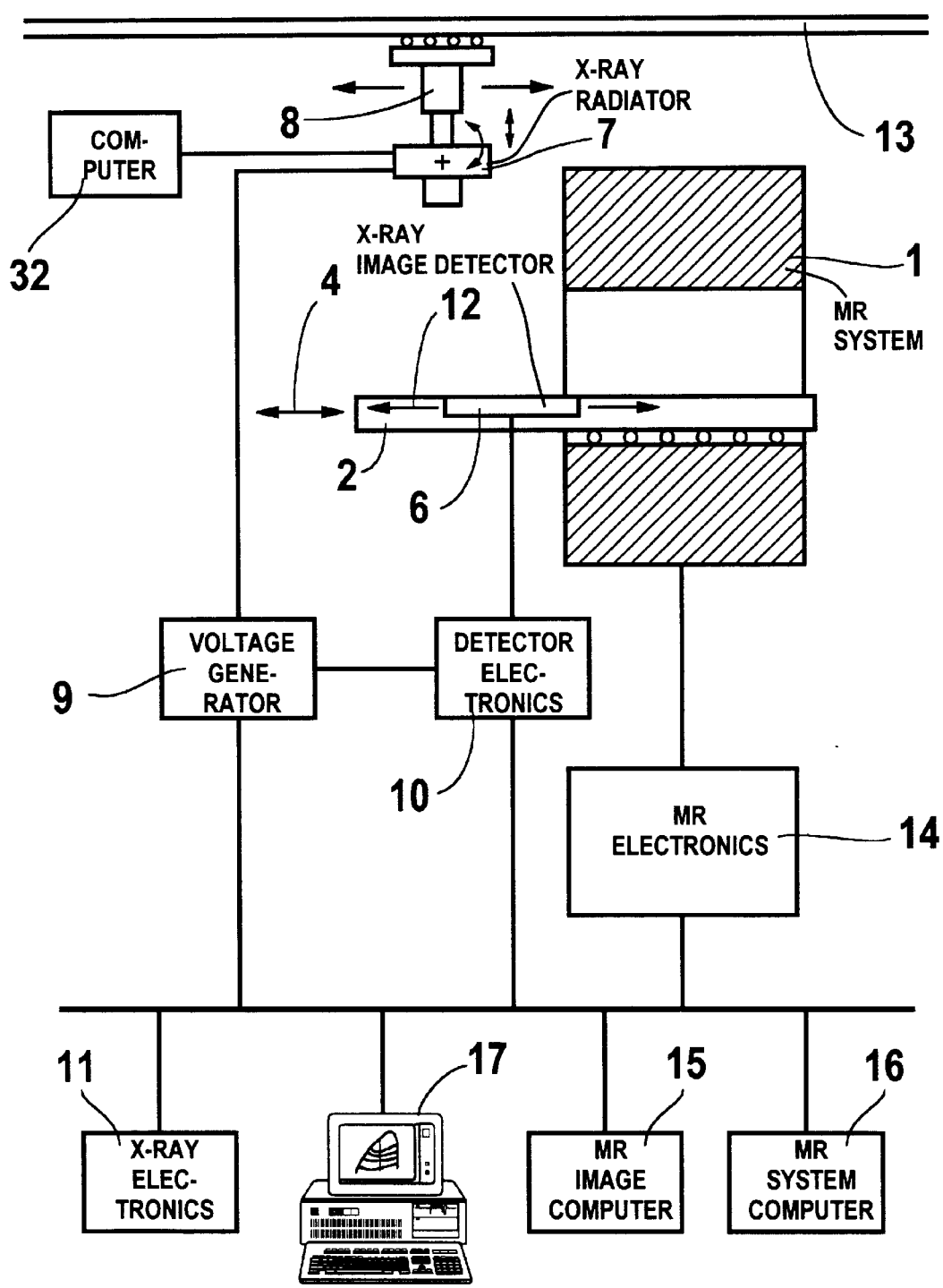
FIG. 2 is a block circuit diagram for the examination installation according to a second embodiment.

FIG. 2 shows a block circuit diagram of applicable to all embodiments, and an alternative arrangement of an MR apparatus 1 with an X-ray device. For preparation of digital X-ray exposures, the digital X-ray image detector 6 is arranged in the patient support 2 so as to be displaceable in the direction of the arrows 12. The X-ray radiator 7 is height-adjustably seated at a ceiling mount 8. The ceiling mount 8 is displaceably attached to the ceiling 13 of the examination room.

Figure 4:
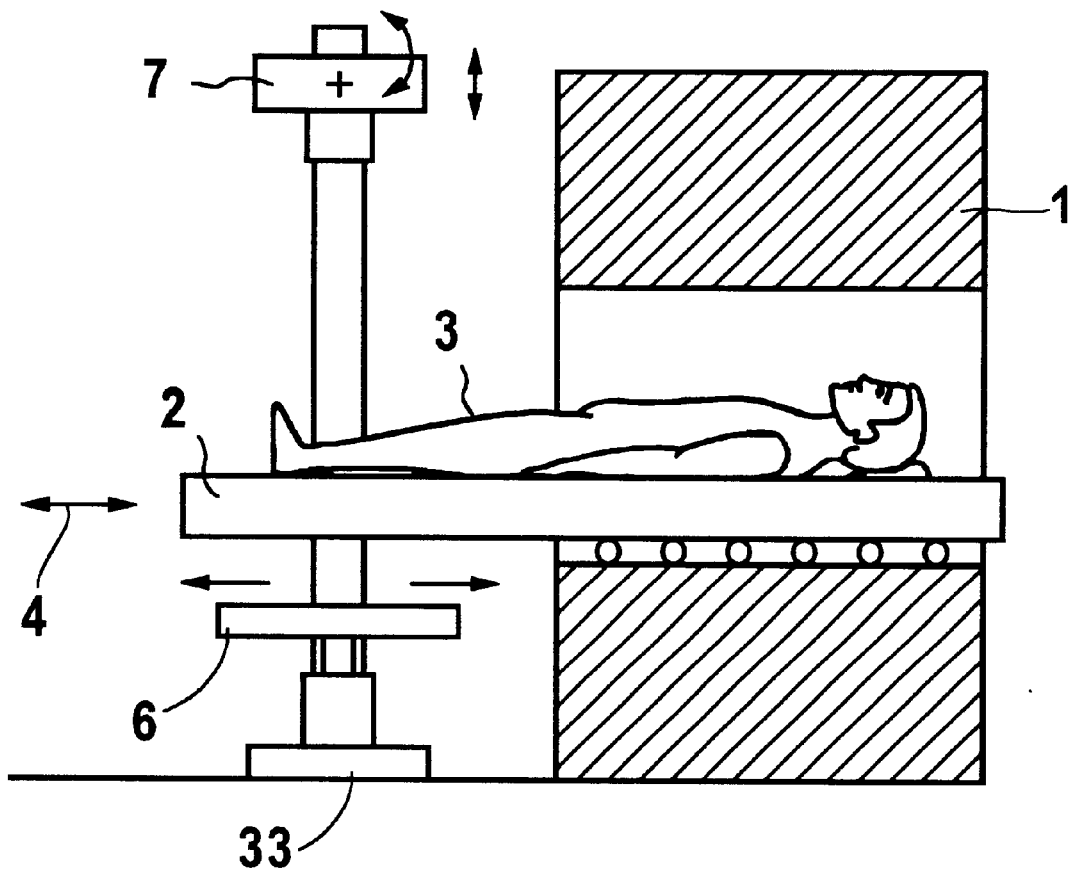
FIG. 4 illustrates a third embodiment of a medical examination installation of the invention with various patient positions.

The digital X-ray image detector 6, however, alternatively can be secured to the wall with a mount or, as shown in FIG. 4, can be secured to the floor of the examination room in freely movable fashion by a mount 33 so that it is height-adjustable and/or displaceable parallel to the examination plane.

The illustrated medical examination installation also has a voltage generator 9, a detector electronics 10 for detector control and image editing, X-ray electronics 11 for controlling the voltage generator 9, an MR electronics 14 for control, pre-amplification, generation and modulation of the RF signals and for gradient control, an MR image computer 15 and an MR system computer 16. Further, a workstation 17 is provided as a common control panel for the playback of the MR image and of the X-ray image having a display monitor for MR and X-ray examinations.

Figure 3:
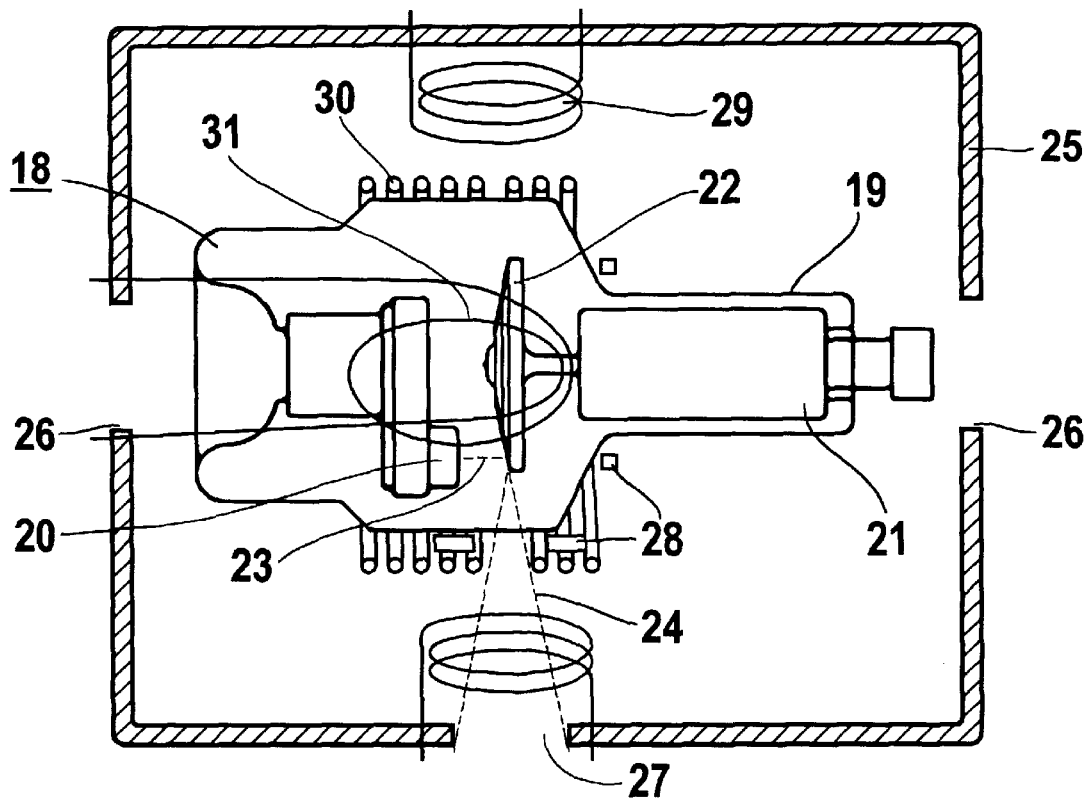
FIG. 3 illustrates the inventive X-ray radiator used in the installation of FIG. 1.

FIG. 3 shows the X-ray radiator 7 of the X-ray system with the X-ray tube 18, a housing 19, a cathode 20 and a rotating anode dish 22 attached to an anode motor 21. In a known way, the electron beam 23 emanates from the cathode 20, producing an X-ray beam 24 after striking the rotating anode dish 22.

The X-ray tube 18 is surrounded by a magnetic shielding 25 that has two openings 26 for the lead-through of the high-voltage connections and a beam exit window 27 for unimpeded passage of the X-ray beam 24 therethrough. Magnetic field sensors 28 for acquiring the remaining, magnetic, location-dependent stray field of the MR system in the three spatial axes are arranged in the proximity of the X-ray tube 18 and the X-ray beam 24.

Instead of the magnetic field sensors 28, location sensors can be utilized that identify the position of the X-ray tube 18 relative to the MR system 1 and calculate the magnetic, location-dependent stray field of the MR system at the location of the X-ray tube 18 on the basis of stored magnetic field profiles.

For compensating the remaining stray field, three coil pairs 29 through 31 arranged in the three spatial axes are arranged within the shielding 25, the current in the coil pairs being adjustable such that the magnetic field they generate cancels out the remaining stray field in the respective spatial axis in the region of the electron beam of the X-ray tube 18. The coil pair 29 serves for compensation in the Y-direction, the divided coil 30 serves this purpose in the X-direction, and the coil pair 31 (only the upper coil is shown) serves for compensation of the residual field in the Z-direction.

The magnetic field sensors 28 acquire the magnetic, location-dependent stray field of the MR system remaining within the magnetic shielding 25 in the three spatial axes, and the values are supplied to a computer 32 shown in FIG. 2. The computer 32 determines the current for the coil pairs 29 through 31 therefrom. Subsequently, the magnetic field sensors 28 again check whether a residual magnetic field is still present and, if necessary the current values for the coil pairs 29 through 31 are reset until the magnetic fields in all three spatial axes have been cancelled.

Instead of the illustrated X-ray devices, one having an "electronic C-arm" can be employed, whereby the X-ray radiator 7 and the solid-state X-ray image detector 6 are mounted independently of one another. Location sensors attached to the X-ray radiator 7 and to the solid-state X-ray image detector 6 serve for determining position and angle. The X-ray radiator 7 and the solid-state X-ray image detector 6 can be aligned to one another and readjusted by motor drives and electronic controls. The measurement sensor mechanism with path sensors and rotational angle sensors thereby monitors the current, exact position of the X-ray system with the X-ray radiator 7 and solid-state X-ray image detector 6 in relationship to the MR apparatus 1 and, in particular, relative to the position of its patient support. As a result, X-ray radiator 7 and the solid-state X-ray image detector 6 can be aligned to one another and can be reliably and precisely moved on the desired paths.

When not being used, the "electronic C-arm" can simply be parked at the MR apparatus and can offer more flexibility, particularly given interventional operations, since no mechanical coupling of the two components of tube and X-ray image detector is required.

Regardless of whether it is a mechanical or an electronic C-arm, the C-arm can be swivelled freely in space around the patient in up to three directions that preferably reside perpendicularly relative to one another. Thus, the optimum X-ray image projection can be set for the particular intervention.

It is important, however, that the exact position of the projection geometry of the X-ray device 5 through 8 is known in relationship to the position of the image acquisition of the MR apparatus 1. For example, a selected X-ray projection plane, established by the focal point of the X-ray tube and two arbitrary image points of the a-Si panel, or where a straight line or a point are respectively located in the X-ray image, can be made visible in the presentation of the stored MR images.

An X-ray image detector on a basis of a-Si panel form a flat surface of the X-ray image detector and, compared to RBV-FS systems, therefore have no distortions of the image geometry. For this reason, such image pickup systems are extremely well-suited for X-ray tomogram applications. A development of classic tomography is tomosynthesis wherein tomograms with a nearly arbitrary slice position and slice height can be subsequently reconstructed from a series of acquired, individual projection images. The spatial information of the tomosynthesis images can be superimposed with the content of the stored MR images by the image fusion technique. As a result, errors can be avoided in the interventional operation and the recovery chances are enhanced because of the increased precision of the intervention despite a faster operating speed.

At least the X-ray radiator 7 must be moved for the acquisition of the multiple projections, for example 4 through 30, required for the tomosynthesis. To that end, the X-ray radiator 7 is advantageously moved on a plane that lies parallel to the sensor plane because the magnification scale of the individual projections then does not differ. The radiator displacement can be very simply realized with the described "electronic C-arm" where there is no fixed mechanical coupling between X-ray source and X-ray image detector. Since the position of the target area of the examination (region of interest, ROI) is usually known, the image receiver can also be moved opposite the radiator movement. An enlarged image field around the ROI is thus obtained.

The direct spatial connection of the MR image acquisition with the X-ray image acquisition given full spatial use possibility enables an improved therapeutic care of patients to be interventionally treated.

Although modifications and changes may be suggested by those skilled in the art, it is the intention of the inventor to embody within the patent warranted hereon all changes and modifications as reasonably and properly come within the scope of his contribution to the art.

I claim:

1. A medical examination installation comprising:
    a magnetic resonance system for obtaining magnetic resonance images of an examination subject, said magnetic resonance system having a stray magnetic field associated therewith;
    an X-ray system having an X-ray radiator containing an X-ray tube, said X-ray tube emitting an electron beam which produces X-rays and a solid state X-ray image detector on which said X-rays are incident for producing a radiological exposure of said examination subject;
    said X-ray system further comprising a plurality of sensors respectively generating output signals which collectively characterize a location dependency of said stray magnetic field in three orthogonal spacial axes, and a plurality of coils for compensating said stray magnetic field; and
    a computer supplied with said output signals from said sensors which calculates respective currents for said coils, and which causes said currents to be supplied to said coils for at least reducing said stray magnetic field in a region of said electron beam of said X-ray tube.

2. A medical examination installation as claimed in claim 1 wherein said plurality of sensors comprise a plurality of magnetic field sensors.

3. A medical examination installation as claimed in claim 1 wherein said X-ray system comprises a magnetic shielding for said X-ray tube, and wherein said plurality of sensors are disposed within said magnetic shielding.

4. A medical examination installation as claimed in claim 1 wherein said plurality of coils comprise three coil pairs, said coil pairs respectively having coil axes which are orthogonal.

5. A medical examination installation as claimed in claim 4 wherein the respective axes of said coil pairs are disposed along said three orthogonal spatial axes.

6. A medical examination installation as claimed in claim 1 wherein said plurality of sensors comprise a plurality of sensors that identify a position of said X-ray tube relative to said magnetic resonance system, and wherein said computer calculates said location dependency of said stray magnetic field from said output signals of said sensors and from magnetic field profiles stored in said computer.

7. A medical examination installation as claimed in claim 1 wherein said X-ray system is attached directly to said magnetic resonance system.

8. A medical examination installation as claimed in claim 1 wherein said X-ray system comprises a C-arm having opposite ends at which said X-ray radiator and said solid state image detector are respectively mounted, said C-arm being attached to said magnetic resonance system.

9. A medical examination installation as claimed in claim 1 wherein said X-ray radiator and said solid state X-ray image detector are respectively mounted on stands disposed next to said magnetic resonance system.

10. A medical examination installation as claimed in claim 1 wherein said X-ray radiator and said solid state image detector are mounted independently of each other, and wherein said X-ray system further comprises a first motor drive for positioning said X-ray radiator and a second motor drive for positioning said solid state X-ray image detector, and a control unit for operating said first and second drives, and wherein said plurality of sensors include X-ray radiator sensors mounted to said X-ray radiator and image detector sensors mounted to said solid state X-ray image detector, and wherein said computer supplies a signal to said control unit for adjusting respective positions and alignment of said X-ray radiator and said solid state image detector relative to each other dependent on said output signals of said plurality of sensors.

11. A medical examination installation as claimed in claim 10 wherein said control unit positions and aligns said X-ray radiator and said X-ray image detector for producing radiological exposures from a plurality of projections for generating a tomosynthesis tomogram of said examination subject, and wherein said medical examination installation further comprises a work station supplied with said tomosynthesis tomogram and with said magnetic resonance image for superimposing said tomosynthesis tomogram and said magnetic resonance image.

12. A medical examination installation as claimed in claim 10 wherein said control unit positions and aligns said X-ray radiator and said X-ray image detector for producing radiological exposures in a plurality of parallel planes for generating a tomosynthesis tomogram of said examination subject, and wherein said medical examination installation further comprises a work station supplied with said tomosynthesis tomogram and with said magnetic resonance image for superimposing said tomosynthesis tomogram and said magnetic resonance image.

13. A medical examination installation as claimed in claim 1 wherein said magnetic resonance system has a patient support adapted to receive said examination subject thereon, and wherein said solid state X-ray image detector is disposed in said patient support and is mounted to so as to be displaceable relative to said patient support.

* * * * *